United States Patent [19]

DeLuca et al.

[11] 4,234,495
[45] Nov. 18, 1980

[54] PROCESS FOR PREPARING 1α-HYDROXYVITAMIN D COMPOUNDS FROM 1α-HYDROXY-3,5-CYCLOVITAMIN D COMPOUNDS

[75] Inventors: Hector F. DeLuca; Heinrich K. Schnoes; David E. Hamer, all of Madison; Herbert E. Paaren, Verona, all of Wis.

[73] Assignee: Wisconsin Alumni Research Foundation, Madison, Wis.

[21] Appl. No.: 73,839

[22] Filed: Sep. 10, 1979

[51] Int. Cl.³ ............................................. C07J 9/00
[52] U.S. Cl. ............................................. 260/397.2
[58] Field of Search ...................................... 260/397.2

[56] References Cited
U.S. PATENT DOCUMENTS

WO 79/00513 9/1979 DeLuca et al. ............ 260/397.2

OTHER PUBLICATIONS

Paaren et al., "Proc. Nat. Acad. Sci." (1978) 75 p. 2080.

*Primary Examiner*—Elbert L. Roberts
*Attorney, Agent, or Firm*—Howard W. Bremer

[57] ABSTRACT

A method for preparing 1α-hydroxyvitamin D compounds from 1α-hydroxy-3,5-cyclovitamin D compounds which comprises solvolyzing the 3,5-cyclovitamin D compound, exposing the solvolysis reaction products to actinic radiation in the presence of a photosensitizing agent and recovering the 1α-hydroxylated vitamin D compounds.

1α-hydroxylation is recognized as being essential to impart biological activity to vitamin D compounds and their derivatives. The present invention provides an efficient method for maximizing the yield of 1α-hydroxylated vitamin D compounds.

12 Claims, No Drawings

PROCESS FOR PREPARING 1α-HYDROXYVITAMIN D COMPOUNDS FROM 1α-HYDROXY-3,5-CYCLOVITAMIN D COMPOUNDS

The invention described herein was made in the course of work under a grant or award from the Department of Health, Education, and Welfare.

DESCRIPTION

Technical Field

This invention relates to the preparation of compounds characterized by vitamin D-like activity. More specifically, this invention relates to 1-hydroxylated vitamin D compounds.

The D vitamins (i.e. vitamin $D_3$ or vitamin $D_2$) are well-known agents for the control of calcium and phosphorus homeostasis. In the normal animal these compounds are known to stimulate intestinal calcium absorption and bone-calcium mobilization, and are effective in preventing rickets. It is also well known that to be effective vitamin $D_3$ (or vitamin $D_2$) must be converted in vivo to its hydroxylated forms. For example, vitamin $D_3$ is first hydroxylated to 25-hydroxyvitamin $D_3$ in the liver, and this intermediate is then further hydroxylated in the kidney to 1α,25-dihydroxyvitamin $D_3$. Vitamin $D_2$ undergoes the same metabolic conversions. The 1α-hydroxylated form of the vitamin is generally considered to be the physiologically active or hormonal form of the vitamin and to be responsible for the various physiological responses mentioned above. It has also been shown that certain unnatural synthetic 1α-hydroxyvitamin D analogs exhibit high biological potency, which in some cases approaches that of the natural forms produced in vivo. Well-known examples are 1α-hydroxyvitamin $D_3$ (U.S. Pat. No. 3,741,996) and 1α-hydroxyvitamin $D_2$ (U.S. Pat. No. 3,907,843) and 3-deoxy-1α-hydroxyvitamin $D_3$ (U.S. Pat. No. 3,906,014).

BACKGROUND ART

Because of the high biological activity of such 1-hydroxylated vitamin D compounds and their potential utility for the treatment of many diseases related to calcium metabolism disorders there has been much interest in chemical processes for their preparation. Almost all of the reported syntheses involve the 1α-hydroxylation of suitable steroids (such as cholesterol) which are subsequently converted to the desired 1α-hydroxyvitamin D compounds (see Schnoes and DeLuca, in Bioorganic Chemistry, vol. 2, Chapter 12, pp. 299-335, edited by E. E. van Tamalen, Academic Press, Inc., New York, 1978).

A novel alternative process introduced recently (Paaren et al, Proc. Nat. Acad. Sci. USA 75, 2080, 1978) entails the preparation of 1α-hydroxyvitamin D compounds by acid catalyzed solvolysis of 1α-0-acyl-3,5-cyclovitamin D compounds which in turn are prepared from 3,5-cyclovitamin D compounds by allylic oxidation and acylation. The process may be illustrated by the following reaction, where R may be any steroid side chain and X is hydrogen or acyl, depending on the solvolysis condition chosen.

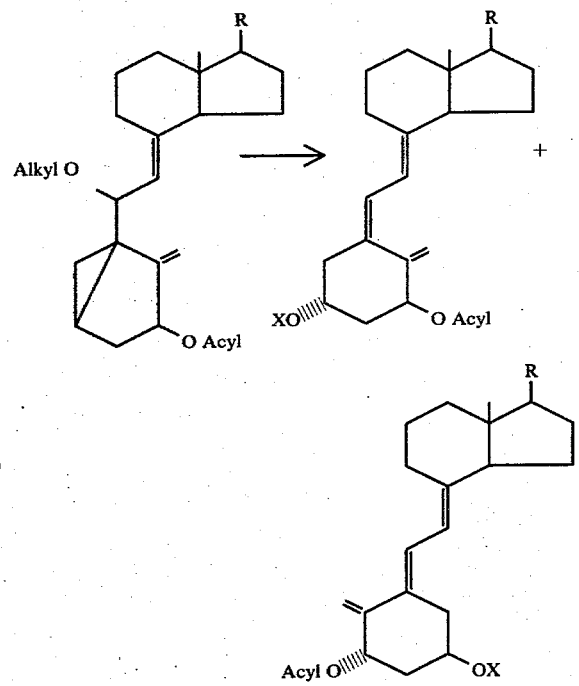

This process however, as shown in the above scheme, leads to both 5,6-cis and 5,6-trans 1α-hydroxyvitamin D compounds (in a ratio of ca. 2:1 to 5:1 depending on conditions) from which the desired 5,6-cis-isomer must be separated by chromatography. Hence, the formation of 5,6-trans compound is a disadvantageous feature of this process (unless 5,6-trans material is desired), which reduces the yield of the desired 1α-hydroxy-5,6-cis-vitamin D compounds.

Disclosure of the Invention

A new process has now been developed which yields the desired 1α-hydroxyvitamin $D_3$ compound (5,6-cis geometry) essentially exclusively, thereby increasing the overall yield of 1-hydroxylated compounds and also avoiding the chromatography step previously required for the separation of 5,6-cis and trans forms. The new process comprises a two-step sequence, involving (1) direct acid catalyzed solvolysis of 1α-hydroxy-3,5-cyclovitamin D compounds, followed by (2) irradiation (photochemical conversion) of the resulting product mixture, and recovering the desired 1α-hydroxyvitamin D compounds (5,6-cis geometry).

Best Mode for Carrying Out the Invention

Suitable starting materials for this process are 1α-hydroxy-3,5-cyclovitamin D compounds of the general formula

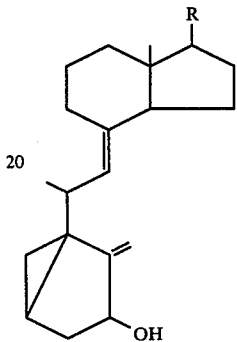

where Z is hydrogen, lower alkyl or acyl, and where the substituent R may be hydrogen or lower alkyl, or may represent any of the common saturated or unsaturated steroid side chains, which may also contain functional groups such as hydroxy, keto, acid or ester groups, as, for example, in the side chains of cholenic acid or its esters, homocholenic acid or its esters, or as in 25-keto- or 24-ketocholesterol.

In the preferred embodiment, R in the above formula is a side chain having the general structure:

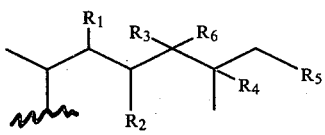

where $R_1$ and $R_2$ are each selected from the group consisting of hydrogen, hydroxy, 0-acyl, 0-lower alkyl and fluoro, or where $R_1$ and $R_2$ together form a double bond or an epoxide grouping, and where each of $R_3$, $R_4$ and $R_5$ is selected from the group consisting of hydrogen, hydroxy, 0-acyl, 0-lower alkyl, lower alkyl and fluoro, and where $R_6$ is hydrogen or lower alkyl.

In this specification and in the claims, "lower alkyl" signifies a hydrocarbon chain of from about 1 to about 5 carbons which may be of straight chain or branched chain configuration, e.g., methyl, ethyl, isopropyl, butyl, etc., and the word "acyl" denotes an aliphatic acyl group of from 1 to 5 carbons, e.g., acetyl, propionyl, butyryl, or an aromatic acyl group such as benzoyl, nitrobenzoyl, or halobenzoyl.

The solvolysis step is conveniently conducted by dissolving the 1α-hydroxy-cyclovitamin D compound of the general structure defined above in a low molecular weight organic acid and briefly heating the solution. Reaction temperatures of 40°-60° C. and reaction times of 15-30 minutes are appropriate. Preferred organic acids are formic, acetic, or trifluoroacetic acid. An organic co-solvent, such as dioxane, or acetone may be used, if convenient, or desirable, to facilitate dissolution of the cyclovitamin starting material.

The photochemical conversion step is effectively conducted by subjecting a solution of the solvolysis product to actinic rays in the presence of a photosensitizer. A light source emitting radiation suitable for the excitation of the photosensitizer is effective, provided that light of wave length less than about 310 mm is excluded, either by suitable filters or by choosing a light source which does not emit radiation below that wave length. In practice, it is convenient to use standard commercial fluorescent lamps for the irradiation, such as the commercial cool white, Models FC12T10/CW, FC8T9/CW, F6T5/CW or F15T8D (all manufactured by Westinghouse Electric Corporation), with suitable filters to effectively eliminate the low ultraviolet radiation component. Pyrex glass is a suitable filter and irradiation of the solution contained in a reaction vessel made of standard Pyrex glass is therefore a practical and advantageous procedure for accomplishing this reaction. Irradiation with standard commercial fluorescent lamps of a solution of the solvolysis reaction mixture in a hydrocarbon solvent such as for example, benzene or toluene, in the presence of a photosensitizer, is a preferred procedure.

During irradiation, the solution is preferably maintained at a temperature below 10° C. under an inert atmosphere e.g., nitrogen or argon. Suitable photosensitizers, such as, anthracene, acridine or phenazine, are added to the solution in about 30-50 fold molar excess relative to the solvolysis product. Irradiation is continued until a photostationary state is achieved, i.e., until there is no further conversion of 5,6-trans to 5,6-cis compound. The progress of the reaction, i.e., decrease of 5,6-trans component and increase of 5,6-cis component is conveniently monitored by analytical thin layer chromatography. Irradiation times of between 5-10 hours are effective, and result in essentially exclusive formation of 1α-hydroxyvitamin D compounds (i.e., 5,6-cis geometry) with only trace amounts of 5,6-trans compound in the final product mixture. Toluene is a preferred solvent because it can be used at temperatures below 5° C., where benzene freezes. Low temperatures and a large excess of photosensitizer facilitate the reaction.

The product, i.e., the desired 1α-hydroxyvitamin D compound, is conveniently isolated in pure form by conventional techniques, e.g., chromatography and subsequent crystallizations from solvents such as ether/pentane mixtures.

It is often advantageous to remove the bulk of the photosensitizer prior to chromatography, e.g. by redissolving the crude mixture after irradiation in a solvent in which the sensitizer is sparingly soluble (e.g., in ethanol or methanol in the case of anthracene) and removing it by simple filtration.

The product obtained from the process of this invention is a 1α-hydroxyvitamin D compound, having the following general structure:

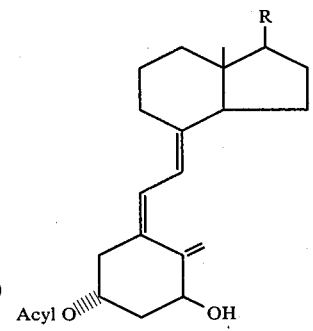

where R is a steroid side chain as defined above, and where the C-3 position carries an 0-acyl group which has been introduced during the solvolysis reaction, the acyl group deriving from the organic acid used in that reaction step (i.e., solvolysis in acetic acid yields 3-acetoxy derivatives, etc).

If the free hydroxy compound is desired the C-3-0-acyl group (and/or any 0-acyl group that may be present in the side chain) is readily removed by conventional techniques, i.e., hydrolysis in methanolic KOH or reduction by hydride reagents, such as lithium aluminum hydride. If desired, of course, the removal of such acyl groups can also be accomplished directly after the solvolysis reaction utilizing the same methods. Subsequent irradiation then yields 1α-hydroxyvitamin D compounds having a C-3-hydroxy substitutent. Both alternatives, i.e., acyl removal before or after irradiation are equally convenient and give identical final product in the same yield.

The present invention offers substantial advantages over the methods of the prior art in that the process yields only the desired 1α-hydroxyvitamin D compounds (5,6-cis geometry) overcoming the simultaneous formation of the corresponding 5,6-trans products as occurs in the method of Paaren et al (reference cited above), thus eliminating the requirement for chromatography to separate the 5,6-cis and trans products which in turn results in significant improvement in the yield of the pure 1α-hydroxyvitamin D product.

Another advantageous feature of the process is its generality which allows, as pointed out above, the application of this two-step method to 1α-hydroxycyclovitamin D starting materials with any of the common steroid side chains. Preferred starting materials are 1α-hydroxy-6-lower alkanoxy-3,5-cyclovitamin $D_3$, 1α,25-dihydroxy-6-lower-alkanoxy-3,5-cyclovitamin $D_3$, 1α,25-dihydroxy-6-loweralkanoxy-3,5-cyclovitamin $D_2$, and 1α,24,25-trihydroxy-6-lower alkanoxy-3,5-cyclovitamin $D_3$, all of which, by the application of the present process are converted to the corresponding 1α-hydroxyvitamin D compounds (5,6-cis geometry).

EXAMPLE 1

Preparation of 1α-Hydroxyvitamin $D_3$ from 1α-Hydroxy-6-Methoxy-3,5-Cyclovitamin $D_3$

Method A

A solution of 50 mg of 1α-hydroxy-6-methoxy-3,5-cyclovitamin $D_3$ in 0.5 ml of glacial acetic acid is heated to 55° C. for 15 min, cooled to room temperature, then added dropwise to a stirring ice/NaHCO₃ mixture. The resulting neutralized suspension is extracted with ether and the organic extracts are washed once with NaHCO₃, once with H₂O, dried over MgSO₄ and concentrated to an oil in vacuo.

The product mixture from the previous reaction is dissolved in toluene (150 ml) in a 500 ml round-bottom flask and a charge of 540 mg of anthracene is added. After cooling to 4° C. the solution is irradiated with two 22 watt fluorescent lamps (Westinghouse FC8T9/CW) under N₂ for 9 h. Isopropanol (250 ml) is added and solvent is removed by azeotropic distillation in vacuo. The residue is suspended in cold methanol and filtered to remove the undissolved anthracene, which is washed with the same solvent. The methanol extracts are concentrated in vacuo and any residual anthracene is removed by percolating the mixture through a short silica gel column eluted first with benzene followed by ethyl acetate.

This material is then dissolved in a small amount of dry ether and treated with an excess of LiAlH₄. After 20 min at room temperature under N₂ the reaction is quenched with 5% NaOH, dried with MgSO₄, and concentrated to dryness in vacuo (31 mg).

Crystallization of the final product 1α-hydroxyvitamin $D_3$, is accomplished from pentane:ethyl ether solutions.

EXAMPLE 2

Preparation of 1α-Hydroxyvitamin $D_3$

Method B

Solvolysis of 1α-hydroxy-6-methoxy-3,5-cyclovitamin $D_3$ (~50 mg) is conducted exactly as described in Example 1. The resulting product mixture is then reduced with LiAlH₄ (ether solvent, 20 min at room temperature under N₂) to convert the 3β-acetoxy function to a 3β-hydroxy group. After standard work-up, the resulting material is then dissolved in 210 ml of toluene, containing 634 mg of anthracene, and irradiated exactly as described in Example 1. After irradiation for 7 hours (at 4° C.), analytical thin layer chromatography (silica gel, ether eluent) shows only a trace of 5,6-trans compound remaining. Isopropanol (240 ml) is added and solvent evaporated. Addition of cold methanol and filtration of the anthracene as described in Example 1, gives, after evaporation of the methanol solvent, a residue which is chromatographed on a silica gel column eluted with benzene and then 1% methanol in chloroform. The product obtained (30 mg) is crystallized from pentane/ether to give crystalline 1α-hydroxyvitamin $D_3$.

What is claimed is:

1. A process for preparing 1α-hydroxyvitamin D compounds which comprises solvolizing, in the presence of an acid catalyst, a 1α-hydroxy-3,5-cyclovitamin D compound corresponding to the 1α-hydroxyvitamin D compound which it is desired to obtain, whereby an 0-acyl group is introduced at least at carbon-3 of the molecule exposing the solvolysis reaction products to actinic radiation in the presence of a photosensitizing agent recovering the 1α-hydroxylated 0-acylated vitamin D product.

2. The process of claim 1 wherein the 1α-hydroxylated 0-acylated vitamin D product is subjected to alkaline hydrolysis or hydride reduction and recovering 1α-hydroxyvitamin D compounds having a free hydroxy group at least at carbon-3 of the molecule.

3. The process of claim 1 wherein the removal of 0-acyl groups is accomplished prior to the irradiation step.

4. The process of claim 1 wherein the solvolysis is conducted in the presence of formic, or acetic acid.

5. The process of claim 1 wherein the photosensitizing agent is selected from the group consisting of anthracene, acridine, and phenazine.

6. The process of claim 5 wherein the photosensitizing agent is anthracene.

7. The process of claim 1 wherein the 1α-hydroxy-3,5-cyclovitamin D compounds being solvolylized have the formula

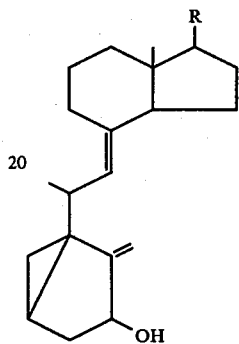

where R is a steroid chain having the structure

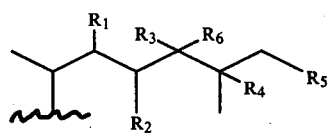

where each of $R_1$ and $R_2$ is selected from the group consisting of hydrogen, hydroxy, 0-acyl, 0-lower alkyl and fluoro, or where $R_1$ and $R_2$ together form a double bond or an epoxide group where each of $R_3$, $R_4$ and $R_5$ is selected from the group consisting of hydrogen, hydroxy, 0-acyl, 0-lower alkyl, lower alkyl and fluoro and where $R_6$ is hydrogen or lower alkyl where Z is hydrogen, lower alkyl or acyl.

8. The process of claim 7 wherein $R_4$ is hydrogen or hydroxy.

9. The process of claim 7 wherein the 1α-hydroxy-3,5-cyclovitamin D compound being solvolyzed is 1α-hydroxy-6-alkanoxy-3,5-cyclovitamin $D_3$.

10. The process of claim 7 wherein the 1α-hydroxy-6-alkanoxy-3,5-cyclovitamin D compound being solvolyzed is 1α,24,25-trihydroxy-6-alkanoxy-3,5-cyclovitamin $D_3$.

11. The process of claim 7 wherein the 1α-hydroxy-6-alkanoxy-3,5-cyclovitamin D compound being solvolyzed is 1α-hydroxy-3,5-cyclovitamin $D_2$.

12. The process of claim 7 wherein the 1α-hydroxy-3,5-cyclovitamin D compounds being solvolyzed is 1α,25-dihydroxy-6-alkanoxy-3,5-cyclovitamin $D_3$ or 1α,25-dihydroxy-6-alkanoxy-3,5-cyclovitamin $D_2$.

* * * * *